United States Patent
Khandke et al.

(10) Patent No.: US 8,540,955 B2
(45) Date of Patent: Sep. 24, 2013

(54) PROCESS FOR PRODUCING ALUMINUM PHOSPHATE

(75) Inventors: Lakshmi Khandke, Nanuet, NY (US); Joseph Perez, Nanuet, NY (US)

(73) Assignee: Wyeth LLC, Madison, NJ (US)

( * ) Notice: Subject to any disclaimer, the term of this patent is extended or adjusted under 35 U.S.C. 154(b) by 1019 days.

(21) Appl. No.: 12/169,665

(22) Filed: Jul. 9, 2008

(65) Prior Publication Data
US 2009/0016946 A1 Jan. 15, 2009

Related U.S. Application Data

(60) Provisional application No. 60/958,958, filed on Jul. 10, 2007.

(51) Int. Cl.
*C01B 25/12* (2006.01)

(52) U.S. Cl.
USPC .......................... 423/304; 423/299

(58) Field of Classification Search
USPC ........................ 423/305, 304, 299
See application file for complete search history.

(56) References Cited

U.S. PATENT DOCUMENTS 2,668,776 A * 2/1954 Miller ........................... 106/443
3,078,215 A   2/1963 Fantes et al.

FOREIGN PATENT DOCUMENTS

GB  777018  6/1957
GB  962182  7/1964

OTHER PUBLICATIONS

Gupta, "Aluminum compounds as vaccine adjuvants," 1998, Advanced Drug Delivery Reviews, 32, pp. 155-172.*
Baylor et al., Aluminum salts in vaccines—US perspective, Vaccine, 2002, s18-23, vol. 20.
Blake, Civil engineer's reference book, Figure 5.29, 1989, Oxford.
Burrell et al., Aluminum phosphate adjuvants prepared by precipitation at constant pH. Part I: composition and structure, Vaccine, 2000, p. 275-81, vol. 19, No. 2-3.
International Search Report and Written Opinion for PCT/US2008/069584 dated Dec. 1, 2008.

* cited by examiner

Primary Examiner — Melvin C Mayes
Assistant Examiner — Melissa Stalder
(74) Attorney, Agent, or Firm — Keith D. Hutchinson; Matthew J. Pugmire (57) ABSTRACT

The present invention provides improved methods for producing the aluminum adjuvant $AlPO_4$. In one aspect, the present invention provides a method for producing aluminum phosphate which comprises the steps of mixing a solution of aluminum chloride and a solution of sodium phosphate tribasic to produce an aluminum phosphate precipitate, wherein the improvement comprises settling the aluminum phosphate precipitate at a temperature in the range of about 50° C. to about 70° C. In another aspect, the present invention is directed to methods for producing aluminum phosphate within a closed system.

12 Claims, 4 Drawing Sheets

PROCESS FOR PRODUCING ALUMINUM PHOSPHATE

PRIORITY INFORMATION

The present application claims the benefit of U.S. Ser. No. 60/958,958, filed Jul. 10, 2007, the entire contents of which are hereby incorporated by reference.

BACKGROUND

Some vaccines and other medicines contain one or more components called adjuvants which serve to enhance the immunogenicity of the vaccine antigens, thereby making the vaccine more effective. Studies have shown that many aluminum-containing vaccines elicit higher and more prolonged antibody responses than the same vaccines formulated without the adjuvant. There are several types of aluminum-containing salts ("also referred to as alum") which function as vaccine adjuvants: (i) aluminum phosphate or $AlPO_4$, (ii) aluminum hydroxide or $Al(OH)_3$, and (iii) potassium aluminum sulfate $AlK(SO_4)_2$. The effectiveness of each aluminum-containing adjuvant often depends on the characteristics of the specific vaccine and how the manufacturer prepares the vaccine (Baylor et al., "Aluminum salts in vaccines-US perspective," *Vaccine* 20:S18-23, 2002). To work as an adjuvant, the antigen typically needs to be adsorbed to the aluminum to keep the antigen at the site of injection.

United States licensed vaccines for children that contain aluminum adjuvants include, without limitation, diphtheria-tetanus-acellular pertussis (DTaP) vaccine, some *Haemophilus influenzae* type b conjugate (Hib) vaccines, Pneumococcal conjugate vaccine, Hepatitis B vaccines, combination DTaP, Tdap, Hepatitis A vaccines, and Human Papillomavirus vaccine.

PREVNAR®, marketed and sold by Wyeth, is a conjugated pneumococcal vaccine that contains aluminum phosphate as an adjuvant. The antigens in PREVNAR® (conjugated pneumococcal vaccine) are a mixture of polysaccharides from seven different serotypes of *Streptococcus pneumoniae* bacteria, each conjugated to the carrier protein $CRM_{197}$. PREVNAR® (conjugated pneumococcal vaccine) is formulated as a clear aqueous liquid containing a colloidal suspension of the antigen—the substance that stimulates the specific protective immune response—adsorbed onto the aluminum adjuvant $AlPO_4$.

While methods of producing aluminum phosphate adjuvant have been described, there remains a need in the art for methods that are more efficient and/or sterile, especially on an industrial scale. In addition, it is desirable that any new method produce aluminum phosphate adjuvant with similar physical, chemical and functional characteristics as the aluminum phosphate adjuvant already in commercial use, e.g., in PREVNAR® (conjugated pneumococcal vaccine).

SUMMARY

The present invention provides improved methods for producing the aluminum adjuvant $AlPO_4$. These improved manufacturing methods benefit from increased efficiency and/or increased sterility as compared to other methods and are particularly useful on an industrial scale.

Thus, in one aspect, the present invention provides a method for producing aluminum phosphate which comprises the steps of mixing a solution of aluminum chloride and a solution of sodium phosphate tribasic to produce an aluminum phosphate precipitate, wherein the improvement comprises settling the aluminum phosphate precipitate at a temperature in the range of about 50° C. to about 70° C.

In another aspect, the present invention is directed to a method for producing aluminum phosphate comprising the steps of: (i) mixing a solution of aluminum chloride and a solution of sodium phosphate tribasic to produce an aluminum phosphate suspension and a supernatant; (ii) settling the aluminum phosphate suspension to produce an aluminum phosphate precipitate; and (iii) removing the supernatant, wherein the steps of mixing, settling and removing are performed within a closed system.

These and other aspects of the present invention will be apparent from the following description and from the claims.

DETAILED DESCRIPTION OF CERTAIN EMBODIMENTS

The present invention provides improved methods for the manufacture of the aluminum adjuvant $AlPO_4$. These methods are especially useful in the industrial-scale manufacture of $AlPO_4$.

Figure 1:
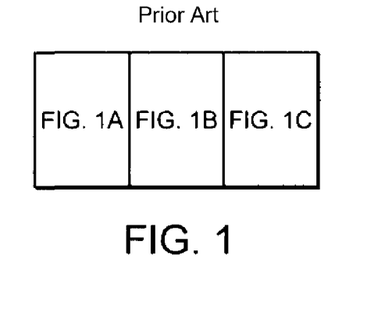
FIG. 1 depicts a flow diagram for a prior art method of producing $AlPO_4$ that has been divided into three parts (FIGS. 1A-C).
Figure 1A:
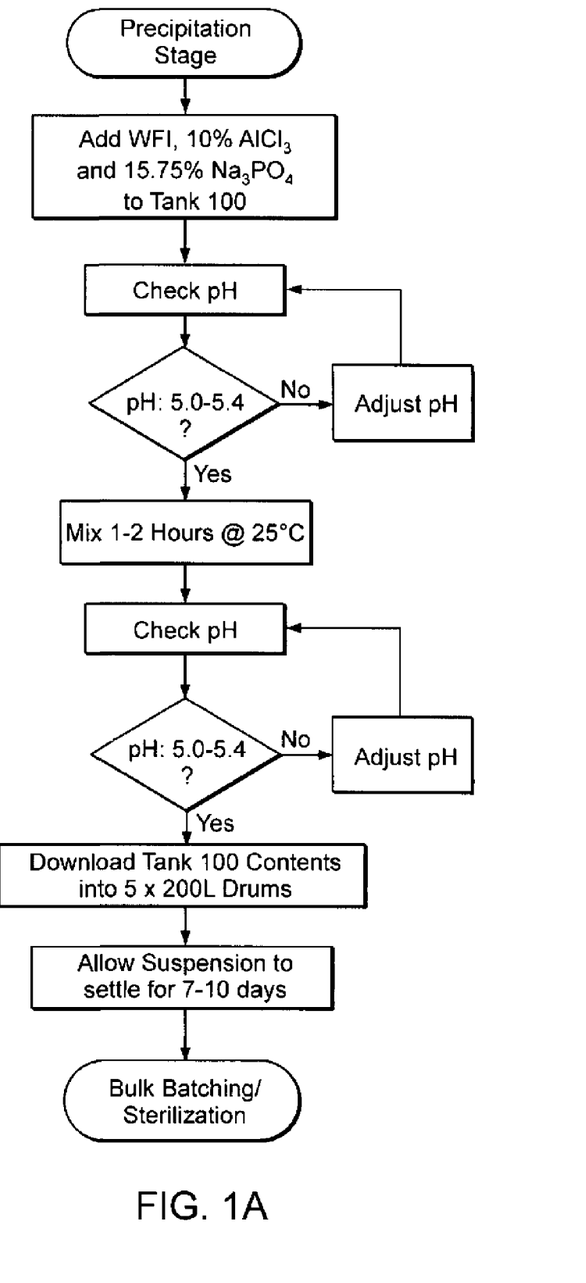
Figure 1B:
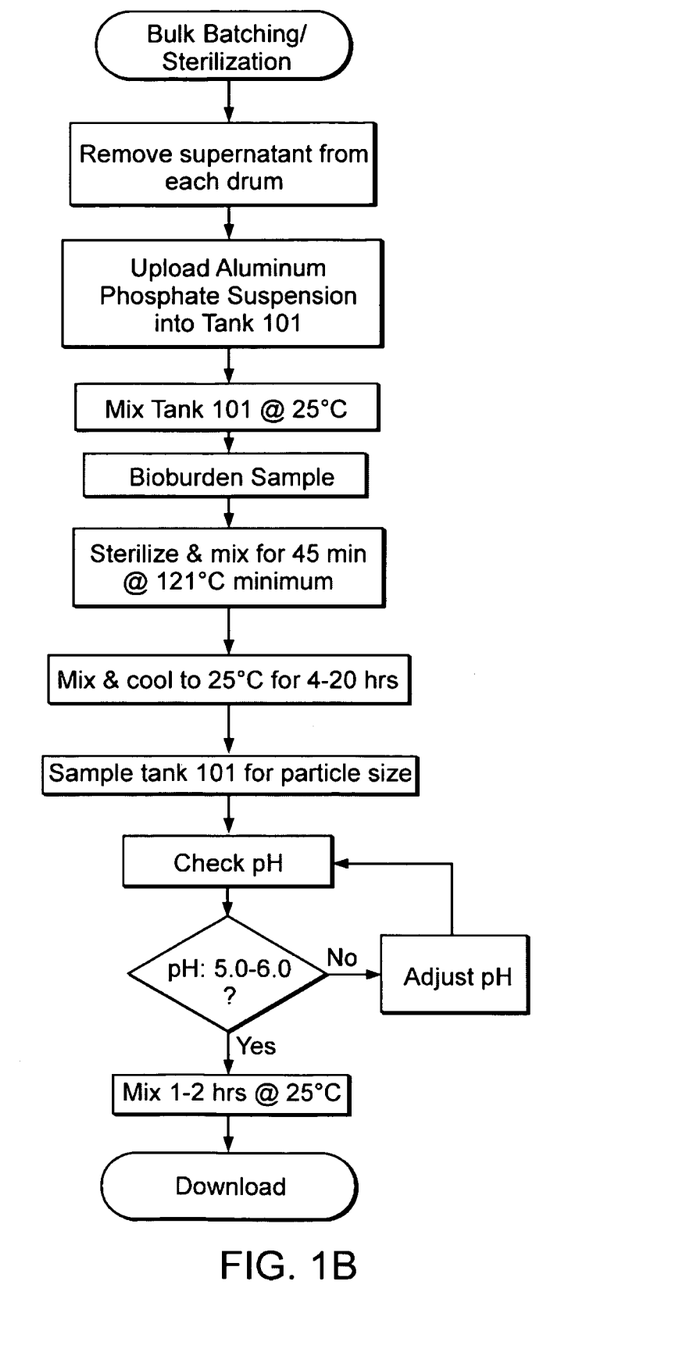
Figure 1C:
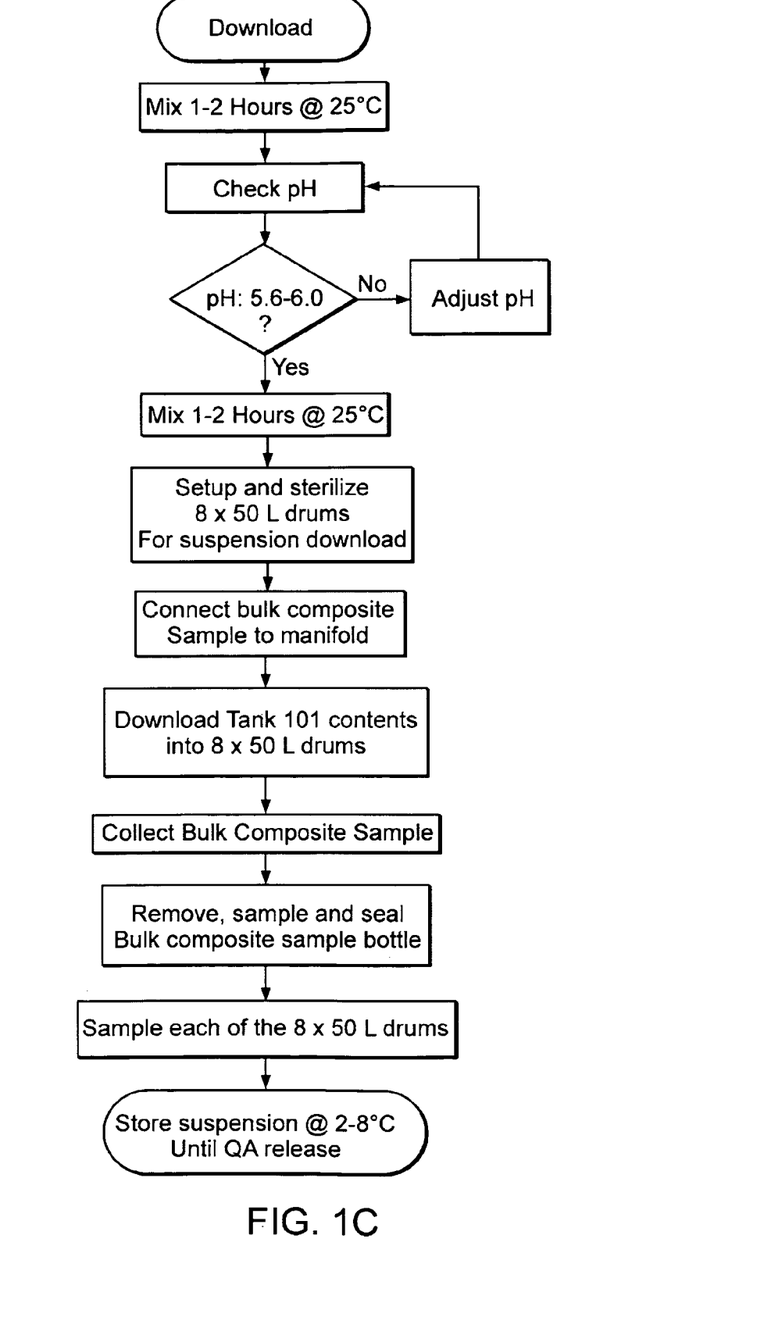

FIG. 1 depicts a method for producing aluminum phosphate in which aluminum chloride ($AlCl_3$) and sodium phosphate tribasic ($Na_3PO_4$) are first prepared separately. The aluminum chloride can be in the form of aluminum chloride hexahydrate. These reagents are then aseptically transferred to a formulation vessel (Tank 100) and combined with water (e.g., water-for-Injection or WFI). The reaction between these reagents results in the formation of an $AlPO_4$ suspension. The suspension is then transferred into drums for settling at 25° C. The settling time for this process (i.e., the time required to allow the $AlPO_4$ precipitate to settle in the drums) is approximately 7 to 10 days which represents the slowest step in the overall process. After settling, the supernatant is removed from each drum and the precipitated $AlPO_4$ is transferred into a formulation vessel (Tank 101) for sterilization-in-place (e.g., $\geq 121°$ C., 45 min) and pH adjustment. The final $AlPO_4$ is then transferred into drums for storage. The total batch cycle time of this method on an industrial scale is approximately 10 to 12 days. In addition, the open nature of this process requires that the multiple aseptic manipulations be performed in a clean air environment (e.g., Class 100). This is costly and also necessitates sterility testing.

Figure 2:
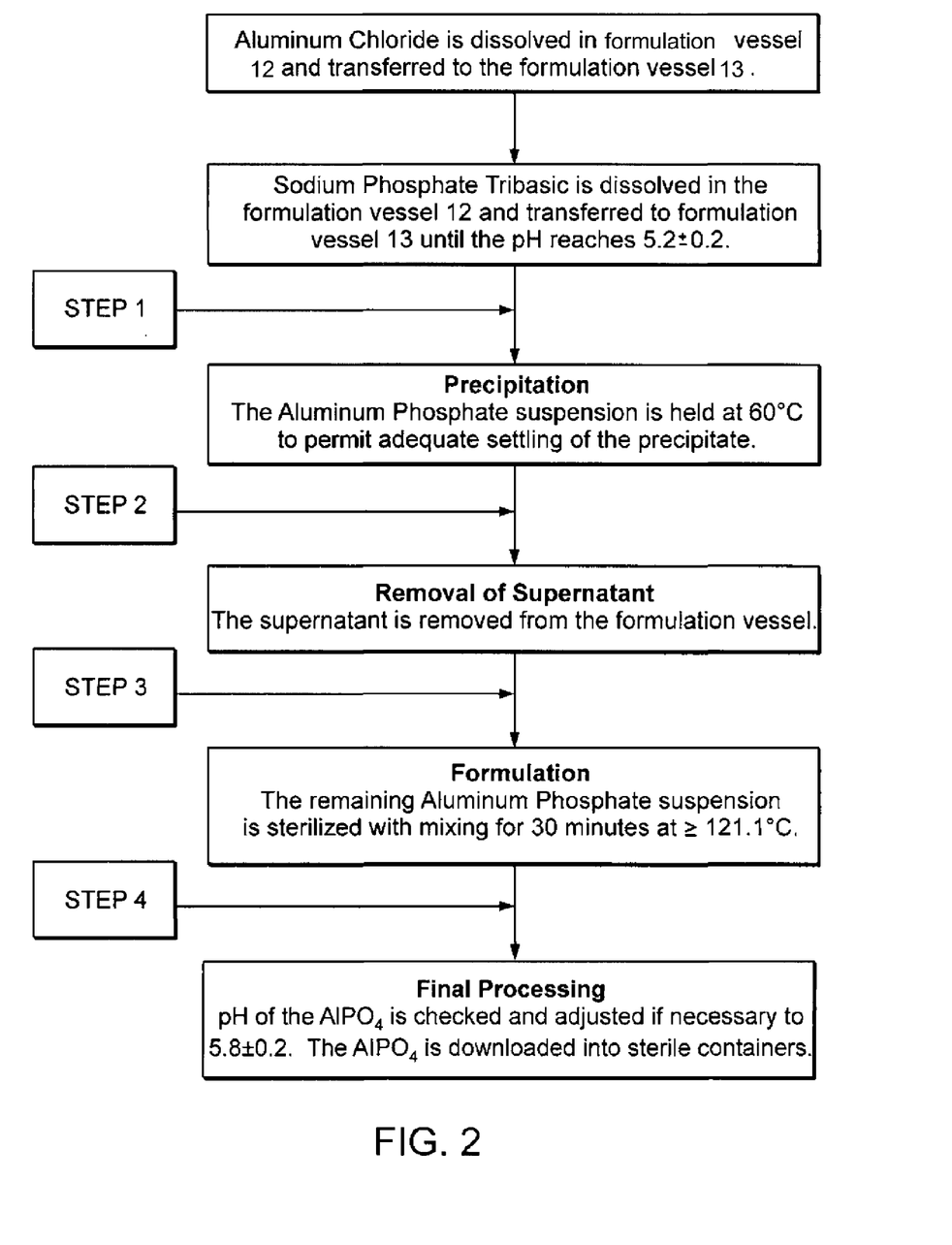
FIG. 2 depicts a flow diagram for an improved method of producing $AlPO_4$.

The efficiency of the method depicted in FIG. 1 is improved significantly by, inter alia, performing the settling step at higher temperatures. In an improved method that is depicted in FIG. 2, after the aluminum chloride, sodium phosphate tribasic and water are mixed to form an $AlPO_4$ suspension, the suspension is allowed to settle at about 50° C. to 70° C. (e.g., 60° C.). The settling time at these higher temperatures is reduced from about 7 to 10 days to between about 2 and 5 days.

Another improvement as compared to the method of FIG. 1 involves performing all of the process steps within a closed system. This has the advantage of reducing the risk of contamination (e.g., from bacteria, etc.) thereby increasing the sterility assurance of the final product and reducing the need for sterility testing. Thus, in FIG. 2, the supernatant is removed from the formulation vessel (e.g., using a dip tube)

and the remaining AlPO$_4$ suspension (still in the same reaction vessel) is sterilized-in-place (e.g., ≧121.1° C., 30 min) before the pH is adjusted. The final AlPO$_4$ product can then be transferred into drums for storage. The total batch cycle time of this method on an industrial scale is approximately 3 to 6 days (i.e., half the cycle time of the method in FIG. 1). A reduced cycle time provides an advantage in efficiency. Table 2 provides a side-by-side comparison of some of the differences between the methods depicted in FIGS. 1 and 2.

Based in part on these findings, the present invention provides a method for producing aluminum phosphate which comprises the steps of mixing a solution of aluminum chloride and a solution of sodium phosphate tribasic to produce an aluminum phosphate precipitate, wherein the improvement comprises settling the aluminum phosphate precipitate at a temperature in the range of about 50° C. to about 70° C. In certain embodiments, the improvement comprises settling the aluminum phosphate precipitate at a temperature in the range of about 55° C. to about 65° C. In another embodiment, the improvement comprises settling the aluminum phosphate precipitate at a temperature of about 62° C. In yet another embodiment, the improvement comprises settling the aluminum phosphate precipitate at a temperature of about 60° C.

As discussed above, these improvements significantly and unexpectedly reduce the aluminum phosphate settling time. For example, in certain embodiments, the settling step may be performed for between about 2 and 5 days as compared to between about 7 and 10 days at lower temperatures. In one set of embodiments, the settling step may be performed for between about 2 and 4 days, e.g., between about 2 and 3 days or between about 3 and 4 days. It will be appreciated that the settling step may be performed for as long as desired within these ranges or even for longer (e.g., 5 or more days) or shorter periods (e.g., less than 2 days). Longer settling periods will generally produce greater yields as compared to shorter settling periods; however, there will also be an efficiency trade-off as a result of the increased duration of the overall manufacturing process. Accordingly, the optimal settling time will need to take both factors into account and will also depend on the exact settling temperature.

In another aspect, the present invention is directed to a method for producing aluminum phosphate within a closed system. The use of the closed system significantly improves the sterility assurance of the process. This makes the overall process more efficient since it reduces the number of sterility tests that need to be performed and no longer requires the process to be performed within a clean air environment. As used herein, the term "closed system" means a system in which exposure of the reaction mixture contained inside one or more vessels to the outside environment (e.g., air, oxygen, microbes, and the like) is reduced or prevented. According to this aspect, the inventive method comprises the steps of (i) mixing a solution of aluminum chloride and a solution of sodium phosphate tribasic to produce an aluminum phosphate suspension and a supernatant; (ii) settling the aluminum phosphate suspension to produce an aluminum phosphate precipitate; and (iii) removing the supernatant, wherein the steps of mixing, settling and removing are performed within a closed system.

In certain embodiments, in the mixing step of the above method, the solution of sodium phosphate tribasic is added to the solution of aluminum chloride. The solution of sodium phosphate tribasic is typically added to the solution of aluminum chloride until the pH is in the range of about 5.0 to about 5.4 (i.e., about 5.2±0.2). In certain embodiments, the solution of sodium phosphate tribasic is added to the solution of aluminum chloride until the pH is in the range of about 5.1 to about 5.3.

In certain embodiments, the mixing step of the above method is performed at a temperature in the range of about 20° C. to about 30° C. In certain embodiments, the mixing step is performed at a temperature of about 25° C.

In certain embodiments, the mixing step of the above method comprises mixing the solution of aluminum chloride and the solution of sodium phosphate tribasic with an impeller rotating at about 150 rpm to about 350 rpm. In certain embodiments, the mixing step of the above method comprises mixing the solution of aluminum chloride and the solution of sodium phosphate tribasic with an impeller rotating at about 200 rpm to about 300 rpm. In yet other embodiments, the mixing step of the above method comprises mixing the solution of aluminum chloride and the solution of sodium phosphate tribasic with an impeller rotating at about 250 rpm.

In certain embodiments, the settling step of the above method is performed at a temperature in the range of about 50° C. to about 70° C., i.e., as described in the first aspect of the invention. In certain embodiments, the settling step of the above method is performed at a temperature in the range of about 55° C. to about 65° C. In another embodiment, the settling step is performed at a temperature of about 62° C. In yet other embodiments, the settling step is performed at a temperature of about 60° C.

In certain embodiments, the settling step may be performed for between about 2 and 5 days. For example, the settling step may be performed for between about 2 and 4 days, e.g., between about 2 and 3 days or between about 3 and 4 days. It will be appreciated that the settling step may be performed for as long as desired within these ranges or even for longer (e.g., 5 or more days) or shorter periods (e.g., less than 2 days).

In certain embodiments, the removing step comprises decanting the supernatant. In certain embodiments, the removing step comprises removing the supernatant using a dip tube.

In certain embodiments, the above method further comprises sterilizing the aluminum phosphate precipitate, wherein the steps of mixing, settling, removing and sterilizing are all performed within a closed system. In certain embodiments, the step of sterilizing comprises heating the aluminum phosphate precipitate to a temperature in excess of about 110° C. In certain embodiments, the step of sterilizing comprises heating the aluminum phosphate precipitate to a temperature in excess of about 121° C.

In certain embodiments, the above method further comprises adjusting the pH of the aluminum phosphate precipitate, wherein the steps of mixing, settling, removing, sterilizing and adjusting are all performed within a closed system. In certain embodiments, the step of adjusting comprises adjusting the pH of the aluminum phosphate precipitate to be in the range of about 5.6 to about 6.0. In certain embodiments, the step of adjusting comprises adjusting the pH of the aluminum phosphate precipitate to be in the range of about 5.7 to about 6.0. In certain embodiments, the step of adjusting comprises adjusting the pH of the aluminum phosphate precipitate to be in the range of about 5.8 to about 6.0. In certain embodiments, the step of adjusting comprises adjusting the pH of the aluminum phosphate precipitate to be in the range of about 5.9 to about 6.0.

The inventive methods may be used to produce aluminum phosphate having a variety of concentrations; however, in certain embodiments, the concentration of aluminum phosphate after the above step of mixing is in the range of about 9.0 to 16.5 mg/ml.

In certain embodiments, after the above step of adjusting the pH, the aluminum phosphate precipitate includes particles with a size distribution having a D[v, 0.5] (definitions of particular size distribution values are set forth in Example 2 below) in the range of about 3.0 µm to about 9.0 µm, or of about 4.5 µm to about 6.5 µm. In certain embodiments, after the above step of adjusting the pH, the aluminum phosphate precipitate includes particles with a size distribution having a D[v, 0.1] of more than about 1.5 µm, or of more than about 2.0 µm. In certain embodiments, after the above step of adjusting the pH, the aluminum phosphate precipitate includes particles with a size distribution having a D[v, 0.9] of less than about 25 µm, of less than about 24 µm, of less than about 23 µm, of less than about 22 µm, of less than about 21 µm, or of less than about 20 µm.

The present invention will be more specifically illustrated with reference to the following examples. However, it should be understood that the present invention is not limited by these examples in any manner.

EXAMPLES

Example 1

System/Process Description

This example describes an exemplary system and process for performing some of the methods that are described herein, such as that depicted in FIG. 2. In this example, the preparation and batching of the manufacturing process of $AlPO_4$ are controlled via a Media Preparation System (MPS or Media Preparation Skid). The MPS consists of 3 batching vessels (50-L, 200-L, and 800-L), filter housings, and piping with sanitary connections. The manufacturing process utilizes both 200-L (V12) and 800-L (V13) vessels. $AlPO_4$ is thereby produced in 800-L (total volume) batches yielding 350-Kg aluminum phosphate precipitate. The final precipitate is downloaded to 50-L drums.

Raw materials used in this process included:
Sodium phosphate tribasic (20.4 Kg)
WFI (for sodium phosphate tribasic dissolution) (107.4 L)
Aluminum chloride hexahydrate (10.1 Kg)
WFI (for Aluminum chloride hexahydrate dissolution) (91.6 L)
5N Sodium hydroxide (for pH adjustment)

The first step in the process was to weigh out 20.4 Kg of sodium phosphate tribasic into the raw material holding container and put it aside. Next, 10.1 Kg of Aluminum chloride hexahydrate was weighed out into a raw material holding container and put aside.

The automated recipe for aluminum phosphate was initiated and the system underwent a pressure test. Vessels V12, V13, and the associated transfer lines were then pre-rinsed with WFI. After the WFI rinse, particulate control filters were placed in-line on both the "filtration side" and "clarification side" of the transfer line between V12 and V13. Prior to sampling bulk, a pre-sterilized sample port with C-FLEX (thermoplastic elastomer tubing) was connected to vessel V13.

The system then underwent another pressure hold test. Upon completion of the pressure hold, the system was flushed with clean steam. After the steam flush, the previously installed filters were flushed with a total of 50-L of WFI.

A target of 162.0-L of WFI was then added to V12. The WFI was then transferred to V13. An additional 100-L of WFI was added to V12 and then transferred to V13. The final critical reaction temperature of 25° C. was established in V13.

A target of 63.0-L of WFI was added to vessel V12. The agitator associated with V12 was started and was controlled to a target of 350 rpm. The pre-weighed aluminum chloride was added to V12 (after a dissolution temperature of 35-45° C. was reached). After the initial dissolution of the aluminum chloride, V12 was brought up to a target of 91.6-L of WFI and mixed for 5-35 minutes prior to visual verification that the aluminum chloride had dissolved. Vessel V13 then began agitating the WFI with a setpoint of 250 rpm. The aluminum chloride was then transferred from V12 to V13.

A target of 150-L of WFI was added to V12. The WFI was then transferred to V13 and additional 150-L of WFI was added to V12 and again transferred to V13. The final critical reaction temperature of 25° C. was established in V13.

A target of 70-L of WFI was added to V12. The agitator associated with V12 was started and was controlled to a target of 350 rpm. The pre-weighed sodium phosphate tribasic was added to V12 (after a dissolution temperature of 35-45° C. was reached). After the initial dissolution of the sodium phosphate tribasic, V12 was brought up to a target of 107.4-L of WFI and mixed for 5-35 minutes prior to visual verification that the sodium phosphate tribasic had dissolved.

The sodium phosphate tribasic was then transferred from V12 to V13 and mixed with the aluminum chloride until a target pH of 5.20 was achieved. After one hour, the pH was again adjusted to a target pH of 5.20 by adding sodium phosphate tribasic. Once the pH was stabilized, the agitator slows to 150 rpm and the temperature setpoint was changed to 60° C. The agitator was turned off after mixing for one hour. The remaining sodium phosphate tribasic was drained from V12, then particulate filters were removed and replaced with CIP caps, and V12 and the transfer lines underwent the CIP procedure.

The aluminum phosphate settled in V13 to below the diptube at a target temperature of 60° C. Once settling was complete (below the diptube), the supernatant was decanted from V13 via the diptube. The sample valve for V13 was then manually sterilized for 15 min at ≧121.1° C. Once the sample valve had been sterilized and cooled to below 60° C., two 25 mL bioburden samples were taken.

The aluminum phosphate in V13 was then sterilized for 30 min at ≧121.1° C. followed by sterilization of the base addition line (15 in at a temp of ≧121.1° C.). Using the sterile connection device, a 1-L bottle of 5N NaOH was connected to the base addition line.

One the aluminum phosphate had cooled to a target temperature of 25° C., the pH of the aluminum phosphate was adjusted to a target of 5.95. Up to 16 pre-cleaned and sterilized 50-L drums were connected to their respective fill stations locations.

The transfer lines were then sterilized for 15 min at ≧121.1° C. The sample valve for V13 was then sterilized for 15 min at ≧121.1° C. Once the sample valve had been sterilized and cooled to less than 60° C., two 30-mL bulk samples were taken for particle size, pH, aluminum concentration, and sterility.

After the samples were taken, the aluminum phosphate was downloaded to the 50-L drums. Once the download was complete, V13 and the transfer lines underwent a full chemical CIP. All of the 50-L drums were then sampled for aluminum concentration and sterility (however, in practice only first and last drums are sampled for sterility). Magnetic stabilizers were affixed to each drum and the drums were stored in a 2-8° C. chill room.

Example 2

Assaying the Physical, Chemical, and Functional Characteristics of AlPO$_4$

Three lots of AlPO$_4$ produced according to the process of FIG. 1 and three lots of material produced according to the process of FIG. 2 (and Example 1) were analyzed to ensure the material produced by both processes were comparable. The assays used were selected based on the physical, chemical and functional characteristics of AlPO$_4$. These characterization studies were performed in addition to the release testing and all lots met the release criteria for AlPO$_4$. The data from the equivalency studies are summarized as follows:

Particle Size Analysis:

Particle size analysis of bulk adjuvants and the formulated vaccine were performed by laser light scattering on a Malvern Instruments Ltd. (Malvern, Worcestershire, UK) particle size analyzer (MASTERSIZER, Serial 2.15). A suspension of powder in a solvent (e.g., isopropanol) was measured with a low angle laser beam, and the particle size distribution was calculated. The volume median diameter D[v,0.5] is the diameter where 50% of the distribution is above and 50% is below the median. Preferably, two determinations of mean particle size should not differ by more than 5% relative. The shape of the curves in the two determinations should also preferably be the same. D[v,0.9] is the diameter where 90% of the volume distribution is below this value. D[v,0.1] is the diameter where 10% of the volume distribution is below this value. The span is the width of the distribution based on the 10%, 50% and 90% quantile (Span={D[v,0.9]−D[v,0.1]}/D[v,0.5]). Prior to each measurement, the instrument was standardized by using beads of a known molecular size representing 2 μm and 10 μm. It was determined that the particle sizes of AlPO$_4$ (before and after formulation into PREVNAR® (conjugated pneumococcal vaccine)) made by both processes were comparable and within the specifications that are listed in Table 1.

TABLE 1

PARTICLE SIZE

| Before formulation | After formulation |
|---|---|
| D[v, 0.1] = ≧2.0 μm | D[v, 0.1] = ≧2.0 μm |
| D[v, 0.5] = 3.7-8.4 μm | D[v, 0.5] = 4.5-6.4 μm |
| D[v, 0.9] = ≦20.0 μm | D[v, 0.9] = ≦22.0 μm |

Protein Binding Assay:

The percent protein bound to AlPO$_4$ was determined by measuring the total protein concentration prior to contact with the aluminum pellet and after treatment with the aluminum pellet. The protein content in the pellet was measured following resuspension in saline. The average percent binding of the carrier protein CRM$_{197}$ formulated with AlPO$_4$ from the process of FIG. 1 (97.5±0.8) and formulated with AlPO$_4$ from the process of FIG. 2 (96.1±1.4) were comparable. The average percent binding of PREVNAR® (conjugated pneumococcal vaccine) formulated with the AlPO$_4$ from the process of FIG. 1 (91.5±1.6) and formulated with AlPO$_4$ from the process of FIG. 2 (91.7±1.9) were also comparable.

Nephelometry Assay:

The vaccine PREVNAR® (conjugated pneumococcal vaccine) was analyzed for antigenicity by nephelometry using citration as a method to solubilize the aluminum pellet. Based on previous work, it is known that only conjugated polysaccharides bind to aluminum and not free polysaccharides or activated saccharides. The antigenicity associated with the pellet reflects polysaccharide that is conjugated. Nephelometry measurements were conducted with the Beckman Array 360 System using antibodies and raised in rabbits. Binding of individual PREVNAR® (conjugated pneumococcal vaccine) conjugates to AlPO$_4$ was measured using nephelometry, and the data for material made using the processes of FIGS. 1 and 2 were found to be comparable.

Zeta Potential/Electrophoretic Mobility:

The zeta potential and electrophoretic mobility were determined using a ZETASIZER (Malvern Instruments Ltd., Malvern, Worcestershire, UK). The zeta potential of AlPO$_4$ from the process of FIG. 1 was an average of 4.7±0.2 mV (5.1±0.1, 3.5±0.2 and 5.5±0.2 mV). The zeta potential of AlPO$_4$ from the process of FIG. 2 was an average of 3.3±0.3 mV (3.6±0.3, 2.6±0.4, and 3.7±0.1 mV).

Settling Time:

Settling time was monitored by measuring the change in the optical density over 30 minutes in a spectrophotometer (Shimadzu UV160-IPC) at a wavelength of 645 nm. The settling time/rate (A$_{645}$/min) of AlPO$_4$ from the process of FIG. 1 was 0.024, 0.025 and 0.023. The settling time/rate (A$_{645}$/min) of AlPO$_4$ from the process of FIG. 2 was 0.027, 0.026 and 0.026.

Table 2 compares some of the parameters that are used in the methods of FIGS. 1 and 2. As shown, the settling time of the aluminum phosphate precipitate was reduced from about 7-10 days to about 2-5 days by increasing the settling temperature from 25° C. to 60° C. This represents a significant improvement in efficiency. As described in Example 1, aluminum phosphate samples produced by both methods have similar physical, chemical and functional characteristics.

TABLE 2

COMPARISON OF PARAMETERS OF TWO METHODS

| Process | FIG. 1 | FIG. 2 |
|---|---|---|
| Reaction temperature | 25° C. | 25° C. |
| Mixing speed during reaction | Rheostat setting at 7/14 | 250 rpm |
| Mixing equipment | Vibromixer | Marine impeller |
| Vessel size/Type for settling | 200 L Drum × 5 | 1000 L Tank-V13 |
| Settling Time | 7-10 days | 62-112 hours |
| Settling Temp | 25° C. | 60° C. |
| Procedure to remove supernatant | Dip tube in drums | Dip tube in Tank |
| Number of tanks in the AlPO$_4$ process | 2 | 2 |
| Upload | Upload AlPO$_4$ from drum to Tank 101 | Not required |
| Mixing speed after supernatant removal | Rheostat setting at 8/93 | 250 rpm |
| Sterilization in place (SIP) conditions | ≧121° C., 45 min | ≧121.1° C., 30 min |

TABLE 2-continued

COMPARISON OF PARAMETERS OF TWO METHODS

| Process | FIG. 1 | FIG. 2 |
|---|---|---|
| Mixing time during final pH adjust | 1-2 hr @ 25° C. | 2-4 hr @ 25° C. |
| Download drum size | 50 L × 8 | 50 L × 13 |
| Sampling System | Closed | Closed |
| Sterility Sampling | All Drums | First and Last Drums |
| Storage temp | 2 to 8° C. | 2 to 8° C. |
| Final in-process pH adjust | 5.6 to 6.0 | 5.6 to 6.0 |

Example 3

Media Simulation

Media simulation studies were performed on the Media Preparation Skid (MPS) of Example 1 using Tryptic Soy Broth (TSB). These studies demonstrated to a high degree of assurance that the sterilizing operations for the MPS maintained sterility and protected against microbial ingress during the manufacture, pH adjustment, sampling and then transfer of sterile solutions into drums. Each media study trial consisted of sterilizing, sterile adjustment of the pH using 5N sodium hydroxide and sterile transfer of the TSB into sixteen drums. The sterile transfer occurred after a $\geq 10$ hour sterile hold. The sterile hold established the total amount of time that the system can be held after the sterilization operations have been performed (11 hours). TSB was collected into a 1 L bottle from all sixteen fill station locations and underwent complete incubation. Samples taken from locations #1 and #16 are representative of the entire solution transfer process into drums. Because of the closed system design of the Media Preparation Skid of Example 1 and the successful results of this study, sterility testing need only be performed on the first and last drums during commercial production, rather than on every drum, as was needed with the method depicted in FIG. 1.

EQUIVALENTS

All material cited in this application, including, but not limited to, patents and patent applications, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present invention has been described in conjunction with various embodiments and examples, it is not intended that the present inventions be limited to such embodiments or examples. On the contrary, the present invention encompasses various alternatives, modifications, and equivalents, as will be appreciated by those of skill in the art.

While the present invention has been particularly shown and described with reference to specific illustrative embodiments, it should be understood that various changes in form and detail may be made without departing from the spirit and scope of the present invention. Therefore, all embodiments that come within the scope and spirit of the present invention, and equivalents thereto, are intended to be claimed. The claims and descriptions of the present invention should not be read as limited to the described order of elements unless otherwise stated.

What is claimed is:

1. A method for producing an aluminum phosphate vaccine adjuvant comprising:
   mixing a solution of aluminum chloride and a solution of sodium phosphate tribasic to produce an aluminum phosphate suspension and a supernatant, wherein the solution of sodium phosphate tribasic is added to the solution of aluminum chloride until the pH is in the range of 5.0 to 5.4;
   settling the aluminum phosphate suspension to produce an aluminum phosphate precipitate, wherein the settling step is performed for a period of about 2 days to about 5 days and at a temperature of about 60° C.;
   removing the supernatant, wherein the steps of mixing, settling and removing are performed within a closed system;
   sterilizing the aluminum phosphate precipitate, wherein the step of sterilizing comprises heating the aluminum phosphate precipitate to a temperature in excess of 110° C.; and
   adjusting the pH of the aluminum phosphate precipitate to be in the range of 5.6 to 6.0, wherein after the step of adjusting the pH, the aluminum phosphate precipitate includes particles with a size distribution having a D [v, 0.5] in the range of 3.0 μm to 9.0 μm.

2. The method of claim 1, wherein the solution of sodium phosphate tribasic is added to the solution of aluminum chloride until the pH of the resulting suspension of aluminum phosphate is in the range of 5.1 to 5.3.

3. The method of claim 1, wherein the mixing step is performed at a temperature of about 25° C.

4. The method of claim 1, wherein the pH of the aluminum phosphate precipitate is adjusted to be in the range of about 5.9 to about 6.0.

5. The method of claim 1, wherein the concentration of aluminum phosphate in the aluminum phosphate suspension after the step of mixing is in the range of about 9.0 to about 16.5 mg/ml.

6. The method of claim 1, wherein after the step of adjusting the pH, the aluminum phosphate precipitate includes particles with a size distribution having a D [v, 0.5] in the range of about 4.5 μm to about 6.5 μm.

7. The method of claim 1, wherein after the step of adjusting the pH, the aluminum phosphate precipitate includes particles with a size distribution having a D [v, 0.1] of more than about 2.0 μm.

8. The method of claim 1, wherein after the step of adjusting the pH, the aluminum phosphate precipitate includes particles with a size distribution having a D [v, 0.9] of less than about 20 μm.

9. The method of claim 1, wherein after the step of adjusting the pH, the aluminum phosphate precipitate includes particles with a size distribution having a D [v, 0.9] of less than about 21 µm.

10. The method of claim 1, wherein after the step of adjusting the pH, the aluminum phosphate precipitate includes particles with a size distribution having a D [v, 0.9] of less than about 22 µm.

11. The method of claim 1, wherein after the step of adjusting the pH, the aluminum phosphate precipitate includes particles with a size distribution having a D [v, 0.9] of less than about 23 µm.

12. The method of claim 1, wherein after the step of adjusting the pH, the aluminum phosphate precipitate includes particles with a size distribution having a D [v, 0.9] of less than about 24 µm.

* * * * *